United States Patent [19]

Feldstein et al.

[11] 4,204,544

[45] May 27, 1980

[54] SIMULTANEOUS MUSCLE FORCE AND DISPLACEMENT TRANSDUCER

[75] Inventors: Cyril Feldstein, Sierra Madre; Gilbert W. Lewis, Arcadia; Virgil H. Culler, La Canada, all of Calif.

[73] Assignee: California Institute of Technology, Pasadena, Calif.

[21] Appl. No.: 838,308

[22] Filed: Sep. 30, 1977

[51] Int. Cl.² .......................... A61B 5/04; A61B 5/10
[52] U.S. Cl. .................................. 128/642; 128/774; 128/782; 33/125 R; 73/781; 338/2
[58] Field of Search .................. 128/2 S, 2 R, 2.06 E, 128/2.1 E, 418, 419 P, 2.1 M, 2.1 C, DIG. 4, 351; 73/88.5 SD, 141 A, 379, 777, 781; 33/125 R, DIG. 13; 126/642, 774, 784; 338/2, 5, 6

[56] References Cited

U.S. PATENT DOCUMENTS

| | | | |
|---|---|---|---|
| 2,406,600 | 8/1946 | Forestiere | 128/2 R |
| 2,815,424 | 12/1957 | Painter | 338/6 |
| 3,263,684 | 8/1966 | Bolton | 128/351 |
| 3,722,005 | 3/1973 | Cowland | 128/418 X |
| 3,905,356 | 9/1975 | Fletcher | 128/2 S |
| 3,937,212 | 2/1976 | Fletcher | 128/2 S |
| 3,971,363 | 7/1976 | Fletcher | 128/2 S |
| 3,971,364 | 7/1976 | Fletcher | 128/2 S |
| 4,135,518 | 1/1979 | Dutcher | 128/418 |

OTHER PUBLICATIONS

Kadefors et al., "A Percutaneous Electrode . . . Humans", Med. & Bio. Eng., vol. 8, No. 2, pp. 129-135, 1970.

Primary Examiner—Lee S. Cohen
Attorney, Agent, or Firm—Freilich, Hornbaker, Wasserman, Rosen & Fernandez

[57] ABSTRACT

A myocardial transducer for simultaneously measuring force and displacement within a very small area of myocardium comprising an elongated body forked at one end to form an inverted Y-shaped beam, each branch of the beam constituting a low-compliant tine for penetrating the myocardium to a predetermined depth. Each tine has a transverse indentation formed around at least a part of it. When the tines are inserted into a heart, the surface membrane of the myocardium closes around the indentations to hold the tines in place. Bonded to one of the low-compliance tines is a small piezoresistive element for converting a force acting on the beam into an electrical signal. A third high-compliant tine of the transducer, which measures displacement of the myocardium in a direction in line with the two low-compliant tines, is of a length that just pierces the surface membrane. A small piezoresistive element is bonded to the third tine at its upper end where its bending is greatest. Displacement of the myocardium causes a deformation in curvature of the third tine, and the second small piezoresistive element bonded to the surface of its curved end converts its deformation into an electrical signal. A separate electrode placed on the epicardium and referenced to the transducer body provides an ECG signal simultaneously with force and displacement signals.

8 Claims, 4 Drawing Figures

U.S. Patent    May 27, 1980    4,204,544
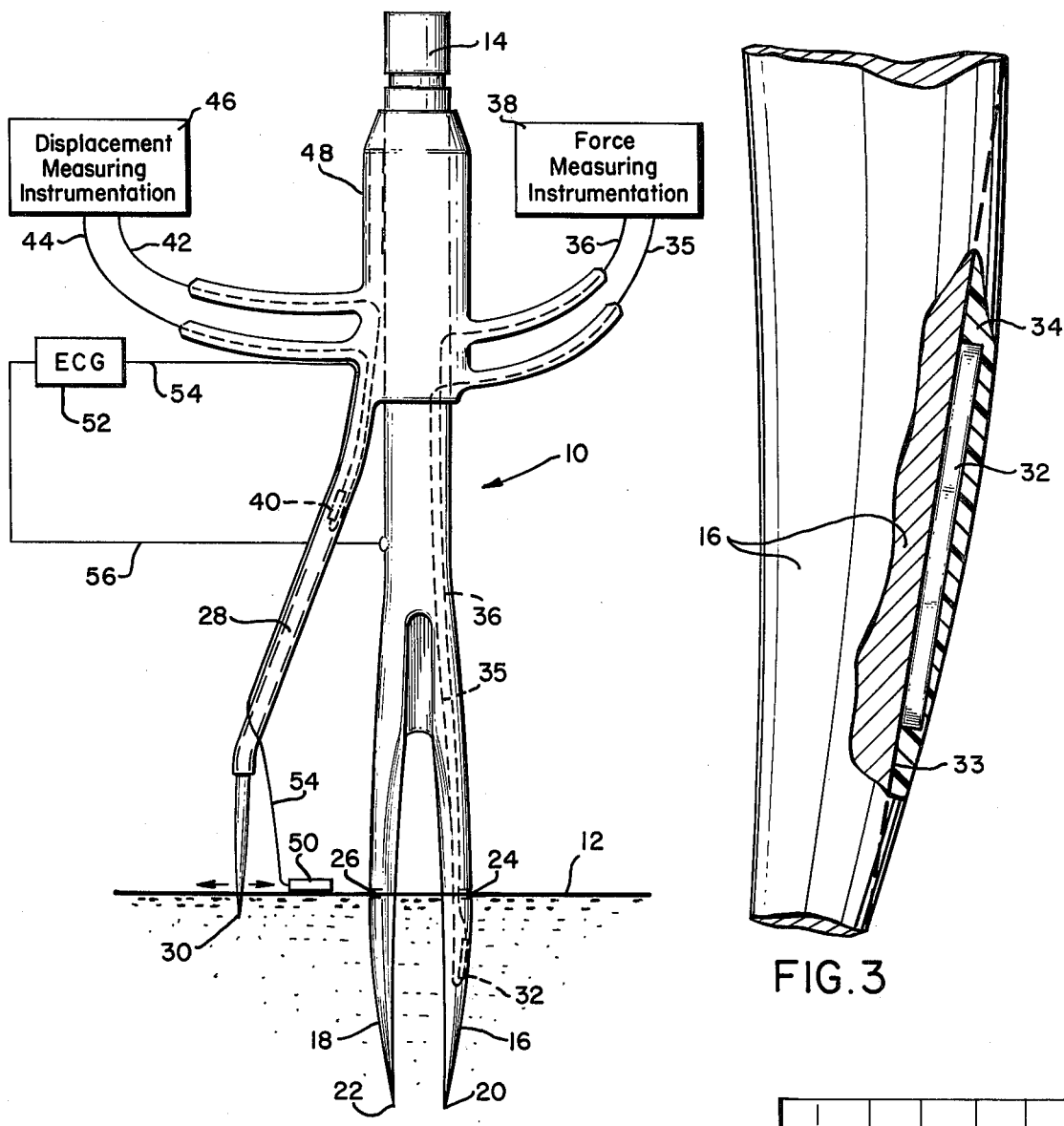
FIG. 1
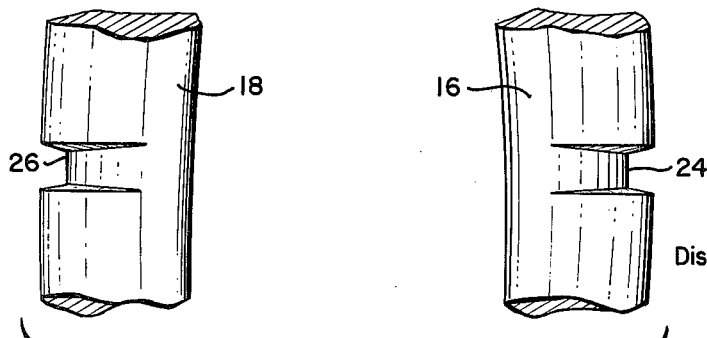
FIG. 2
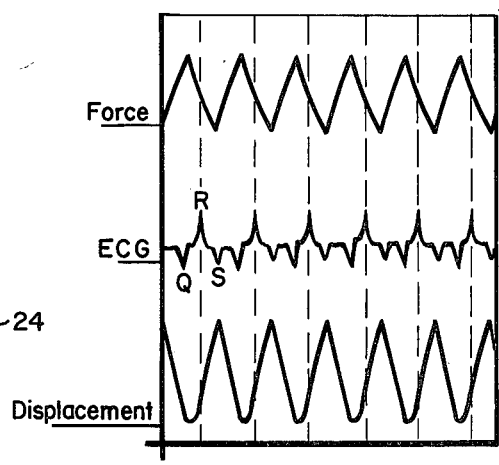
FIG. 3
FIG. 4

SIMULTANEOUS MUSCLE FORCE AND DISPLACEMENT TRANSDUCER

ORIGIN OF THE INVENTION

The invention described herein was made in the performance of work under a NASA contract and is subject to the provisions of Section 305 of the National Aeronautics and Space Act of 1958, Public Law 85–568 (72 Stat. 435; 42 USC 2457).

BACKGROUND OF THE INVENTION

This invention relates to muscle force and dispalcement transducers, and more particularly to a combination whereby measurements can be taken simultaneously of force and displacement within a very small area of the myocardium, and if desired an ECG can be taken in the same area.

Development of cardiac force transducers has been of growing interest for more than a decade. See "Auxotonic and Isometric Cardiac Force Transducers," by Eric O. Feigl, et al., *Journal of Applied Physiology*, Vol. 23, No. 4, October 1967, and references cited therein. There has also been an interest in measuring myocardian displacement. See U.S. Pat. No. 3,937,212 for a Miniature Muscle Displacement Transducer, issued on an invention made by Cyril Feldstein, et al. Now simultaneous measurements of myocardial force and displacement in a very small localized area parallel to subsurface fibers is becoming of interest to research scientists in the field of cardiology. For example, if both force and displacement can be measured simultaneously in a small area, the work being performed by the myocardium in that small area can be determined. It is also of interest simultaneously to provide an ECG as a reference for the heartbeat cycles at the same small area.

Work is directly determined by simultaneous measurement of force, F, and displacement, s, from the relationship between the force exerted on a body and the distance that the body moves in a direction of the force in producing work, W. That relationship is given by the equation $$W = F \times s \cos \theta$$

where $\theta$ is the angle between the direction of the force and the direction of the displacement. Orientation of myocardial fiber may be easily determined in a particular area by measuring force in all different directions to find that direction which yields the greatest measuremet. Once that orientation is determined, force and displacement may be measured simultaneously unmder a condition where $\cos \theta = 1$ by placing all three tines in a line in the direction of fiber orientation. In other words, to measure work directly, it is desirable to measure force and displacement in the same direction as the fiber orientation. The product, W, will be a maximum when that measurement direction is parallel to the fiber orientation in the given localized area.

In the past, myocardial force or tension has been measured by a strain gauge sutured to the epicardial fibers. This has not been ideal because the measurements are too dependent on how tight and deep the sutures are made. Moreover, suturing is time consuming and traumatic to the myocardium, and sutured transducers are difficult to remove. In any case, the same suturing is hard to reproduce from one experiment to another, thus making it virtually impossible to compare data. As pointed out by Feigl, et al., supra, it is preferable to insert pins into the myocardium to measure the force acting on the pins, but still sutures are used to hold the transducer in place.

For measuring displacement, U.S. Pat. No. 3,937,212 cited above shows a transducer comprised of a curved beam of high elastic compliance connected at each end to a pin inserted into the myocardium. A piezoresistive element bonded to the curved beam then measures myocardial displacement between the pins. Because this transducer is intended to measure displacement only, it does not provide any force measurement in the same area as the displacement measurement. There is also the problem of holding the pins in. It would be feasible to provide a barb at the tip of each pin, as shown for the subminiature insertable force transducer disclosed in U.S. Pat. No. 3,905,536, but then the pins cannot be removed without tearing and cutting the myocardial tissue.

OBJECTS AND SUMMARY OF THE INVENTION

An object of this invention is to provide a transducer which will measure muscle force and displacement simultaneously.

Another object is to provide an improved structure for anchoring transducer pins in muscle tissue.

Still another object is to provide a myocardial transducer which will provide an electrocardiograph (ECG) output in conjunction with simultaneous force and/or displacement measurements in a small area.

These and other objects and advantages are achieved in a transducer for measuring force and displacement simultaneously within a very small myocardial or other muscle area comprised of an elongated body with a longitudinal slot at one end forming an inverted, Y-shaped beam of low compliance, each forked branch of the beam constituting a tine. Each of the two tines has a pointed end to facilitate its being easily inserted through the epicardial tissue or the endocardial tissue to a predetermined depth. A transverse slot or identation around at least part of each tine allows tissue to close around the indentation, thus providing improved retention of a transducer having tines, or pins, inserted into the myocardium. A piezoresistive element is bonded to one of the two tines to measure myocardial forces between the tines. The element is preferably bonded in a recessed position on the tine between its tip and indentation so that it is embedded in tissue during the force measurements. A high-compliant tine extends from the upper end of the cylindrical body to just below the level of the indentations in the low-compliant tines. When the transducer is inserted into the myocardium to at least the depth of the indentations of the low-compliant tines, the pointed tip of the third high-compliant tine penetrates the surface membrane. This high-compliant tine has a piezoresistive element bonded to its upper end for measurement of its displacement relative to the low-compliant tines. The third tine is in the same plane as the two low-compliant tines so that displacement is measured in the same direction that the force is being measured. With the body of the transducer acting as one electrode, and a second electrode attached to but electrically isolated from the transducer body, and ECG can be taken in the same area of the myocardium where the force and displacement measurements are made.

BRIEF DESCRIPTION OF THE DRAWINGS

FIG. 1 is a view in elevation of a new transducer according to the present invention.

FIG. 2 is an enlarged view of a portion of FIG. 1.

FIG. 3 is another enlarged portion of FIG. 1.

FIG. 4 is a graph of measurements made with an ECG.

DESCRIPTION OF PREFERRED EMBODIMENTS

Referring now to the drawings, the new transducer 10 is shown piercing the surface membrane 12 of an exposed heart or other muscle. The novel features of the transducer will be described with reference to this mode of its use on the heart muscle, but it should be understood that it could be used on other muscles, or inside the heart using a catheter. In either case, the new transducer provides for the simultaneous mesurement of force and displacement in a small area of the myocardium.

The transducer is comprised of an elongated body 14 slotted at its lower end to form an inverted, Y-shaped beam of low compliance. The two branches 16 and 18 of the beam form low-compliant tines that are shaped into a sharp point at their tips 20 and 22, and slotted around most of their circumferences to form indentations 24 and 26 at a predetermined level of penetration into the myocardium, as shown in the enlarged fragmentary view in FIG. 2. The epicardium 12 will thus close around the indentations 24 and 26 to retain the tips of the tines embedded in the myocardium.

A third tine 28 is in the form of a long beam having high compliance is connected to the upper end of the body 14. When the transducer is inserted into the myocardium such that the epicardium 12 closes on the indentations 24 and 26, a sharp tip 30 of the third tine penetrates the epicardium. Thus, while the two tines forming the inverted Y-shaped beam of low compliance sense the force field in a small area, and in the direction between the two tines, the third tine senses the displacement of the myocardium between the third tine and the closest of the other two tines. All three tines are in the same plane, the plane of the drawing, so that the displacement sensed is in the same direction as the force sensed. The product is thus a measure of work, and as noted hereinbefore, is a maximum when the plane of the tines is parallel to the myocardial fibers. This new transducer may thus be used, for example, to map the direction of myocardial fibers over different areas of the heart.

A piezoresistive element 32 is bonded to one of the two low-compliant tines of the inverted Y-shaped beam in order to convert the force sensed into an electrical signal. The composition and use of piezoresistive materials in transducers are well known to those skilled in the art. See "Semiconducting Stress Transducers Utilizing the Transverse and Shear Piezoresistance Effects," by W. G. Pfann and, R. N. Turner, *Journal of Applied Physics*, Vol. 32, No. 10, pp. 2008–2019, October 1961. The element 32 is mounted on a recessed surface 33, and coated with a protective layer 34 of insulating material, such as the same epoxy used for bonding, so that the mounted element will be effectively flush with the surface of the tine. Attached to the ends of the element are thin insulated leads 35 and 36 which are bonded to the surface of the tine up to the top of the body 14. These leads, shown in dotted line because they are coated with epoxy, are connected to instrumentation 38 for displaying and/or recording the force signal from the piezoresistive element 32.

A piezoresistive element 40 is similarly bonded to the third tine at its upper end. Thin insulated leads 42 and 44 from the ends of the element 40 are bonded to the third tine and the upper body 14 of the transducer. These leads are connected to instrumentation 46 for displaying and/or recording the displacement signal from the element 40. Both of these leads are reinforced and further secured to the body 14 at the point where they depart from the body by a plastic coating 48 as shown. Similarly, an electrode 50 placed on the surface membrane is connected to an ECG instrument 52 by a thin lead 54. A thin return lead 56 from the ECG instrument is connected to the elongated body of the transducer. Both of these leads may be secured to the body and third tine, or either of the tines 16 and 18 in the same manner as other leads, particularly where force and displacement measurements are conditioned for displaying and/or recording together with the ECG on the same time reference. FIG. 4 illustrates idealized traces recorded for several heart beat cycles.

The two tines of the inverted Y-shaped beam are, typically about 8 mm long and 1 mm apart at their tips. The indentation on each tine is about 5 mm from its tip. The tip of the third tine is about 3.5 mm from the tine 18. The length of the third tine, which is mounted higher on the elongated body, is about 13 mm. All of the other dimensions are proportional in the greatly-enlarged drawing. However, it should be understood that these dimensions are given by way of example only. None of these dimensions or proportions ae critical; it is simply important that the total distance from the third tine 28 and the first tine 16 be very small (about 5.5 mm) in order that the force and displacement measurements be made over a very small area. No other transducer is known that will provide force and/or displacement measurements over such a small area, particularly of both force and displacement. In addition no other transducer provides ECG measurements in the same small area where force and displacement are being measured.

Although particular embodiments of the invention have been described and illustrated herein, it is recognized that modifications and equivalents may readily occur to those skilled in the art and consequently it is intended that the claims be interpreted to cover such modifications and equivalents.

What is claimed is:

1. A transducer for use with instrumentation for simultaneously measuring muscle force and displacement comprising:

an elongated body slotted at its lower end to form an inverted Y-shaped beam having first and second tines, said tines being tapered into sharp points to facilitate insertion of said tines into muscle, said tines having a low degree of elastic compliance;

a first piezoresistive element bonded to one of said first and second tines, said first piezoresistive element sensing force acting on said beam through said tines for measurement of muscle force in a direction in line with said tines;

a third tine connected to said body, said third tine being tapered into a sharp point at its free end, and said third tine having a high degree of elastic compliance for measuring displacements of said muscle relative to said first and second tines, said third tine being connected to said body in a position to allow the point thereof to pierce said muscle when said first and second tines are inserted into said muscle;

a second small piezoresistive element bonded to said third tine, said second piezoresistive element sensing muscle displacement relative to said first and second tines; and means for connecting said first piezoresistive element and said second piezoresistive element to said instrumentation.

2. A transducer as defined in claim 1 wherein said third tine extends from said body to place its sharp point in line with the sharp points of said first and second tines.

3. A transducer as defined in claim 2 wherein said first and second tines have indentations spaced from their sharp points such that muscle tissue will close around said indentations to maintain said first and second tines in position when inserted into said muscle.

4. A transducer as defined in claim 3 wherein said third tine extends to a level just below said indentations of said first and second tines.

5. A transducer as defined in claim 1 in combination with said instrumentation and an electrode for placement on the muscle surface membrane, said instrumentation having means for recording an electrocardiogram, and means for connecting said recording means to said electrode and said transducer body for recording said electrocardiogram.

6. A myocaridal transducer for simultaneously sensing force and displacement within a very small area of myocardium comprising an elongated body forked at one end to form an inverted Y-shaped beam, each branch of the beam constituting a low-compliant tine for penetrating myocardium, a piezoresistive element bonded to one of the low-compliant tines for converting a force acting on the beam into an electrical signal, a third high-compliant tine connected to said body of the transducer for sensing displacement of the myocardium in a direction in line with the two low-compliant tines, said third tine extending from said body a length just sufficient for its free end to pierce the surface of said myocardium when the two low-compliant tines are inserted into the myocardium to a predetermined depth, a small piezoresistive element bonded to the third high-compliant tine at a location remote from its free end where its bending is greatest for converting displacement of the myocardium into an electrical signal.

7. The combination of claim 6 including an ECG instrument having a signal input lead and a reference potential lead connected thereto, a separate electrode connected to said signal input lead and adapted to be placed on the surface of the myocardium and said reference potential lead being connected to the transducer body for providing and ECG signal simultaneously with force and displacement signals.

8. A myocardial transducer as defined in claim 6 or 7 wherein each of said low-compliant tines of said inverted Y-shaped beam has indentations spaced from the free end thereof such that the surface of the myocardium will close around said indentations when inserted to hold the tines in place with the third tine just piercing the myocardium.

* * * * *